United States Patent [19]

Standish et al.

[11] 4,069,703

[45] Jan. 24, 1978

[54] PLASTIC ORIENTATION MEASUREMENT INSTRUMENT

[75] Inventors: Norman W. Standish, Shaker Heights; Herbert Talsma, East Cleveland, both of Ohio

[73] Assignee: Standard Oil Company, Cleveland, Ohio

[21] Appl. No.: 718,153

[22] Filed: Aug. 26, 1976

[51] Int. Cl.² .......................................... G01N 25/16
[52] U.S. Cl. ...................................................... 73/16
[58] Field of Search ................................. 73/15.6, 16

[56] References Cited

U.S. PATENT DOCUMENTS

| 2,732,708 | 1/1956 | Linhorst | 73/15.6 |
| 3,010,307 | 11/1961 | Schwegler | 73/15.6 |
| 3,234,778 | 2/1966 | Kreglo | 73/15.6 |
| 3,324,713 | 6/1967 | Krock et al. | 73/15.6 |
| 3,474,658 | 10/1969 | Levy et al. | 73/16 |
| 3,521,477 | 7/1970 | Dollet | 73/15.6 |

OTHER PUBLICATIONS

Davies et al. "A Simple Apparatus for Carrying Out Tensile Creep Tests on Brittle Materials up to Temps. of 1750° C" in J. Phys E. Sci. vol. 4, #6, 6/71, pp. 421–424.

Primary Examiner—Herbert Goldstein
Attorney, Agent, or Firm—John F. Jones; Larry W. Evans

[57] ABSTRACT

An apparatus for measuring degree of orientation in small oriented plastic samples which operates on the principle of measurement of dimensional changes in the samples before, during and after they pass through the temperature range at which the samples' relax is described.

4 Claims, 5 Drawing Figures

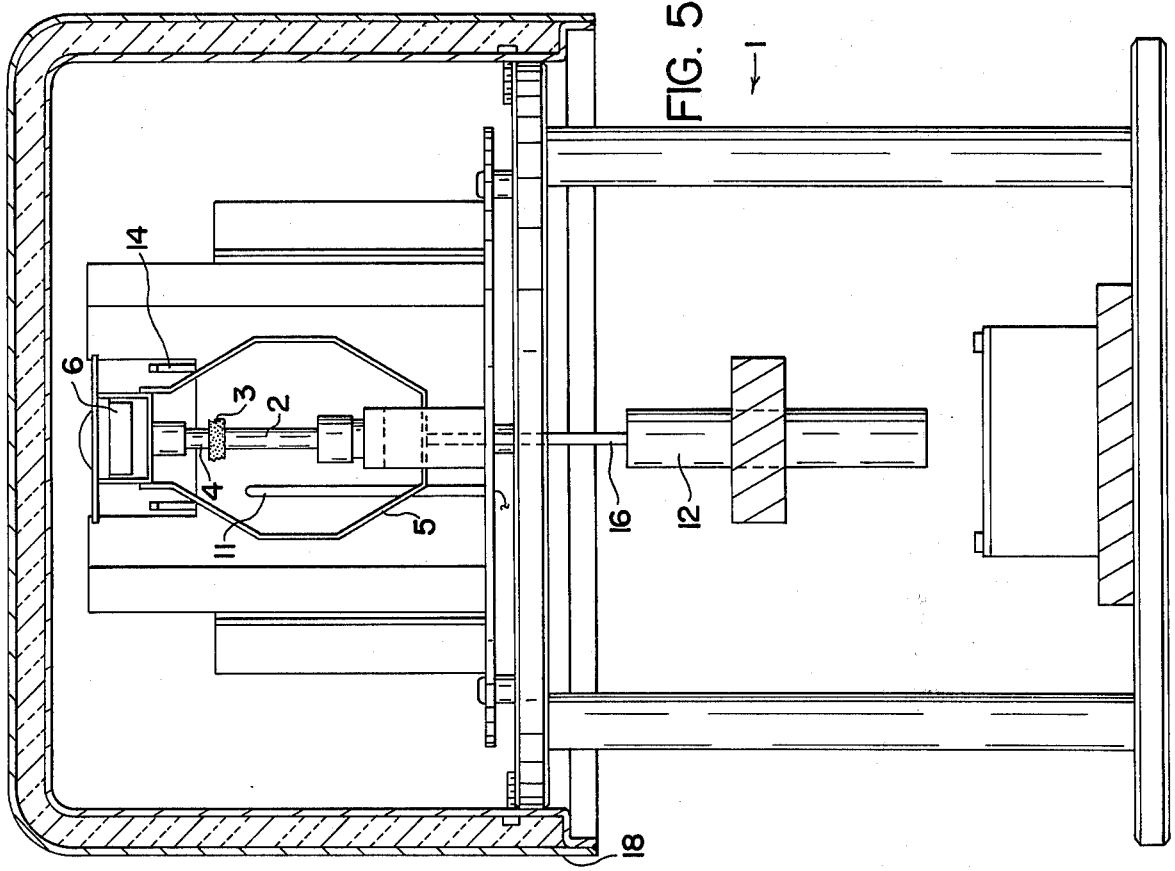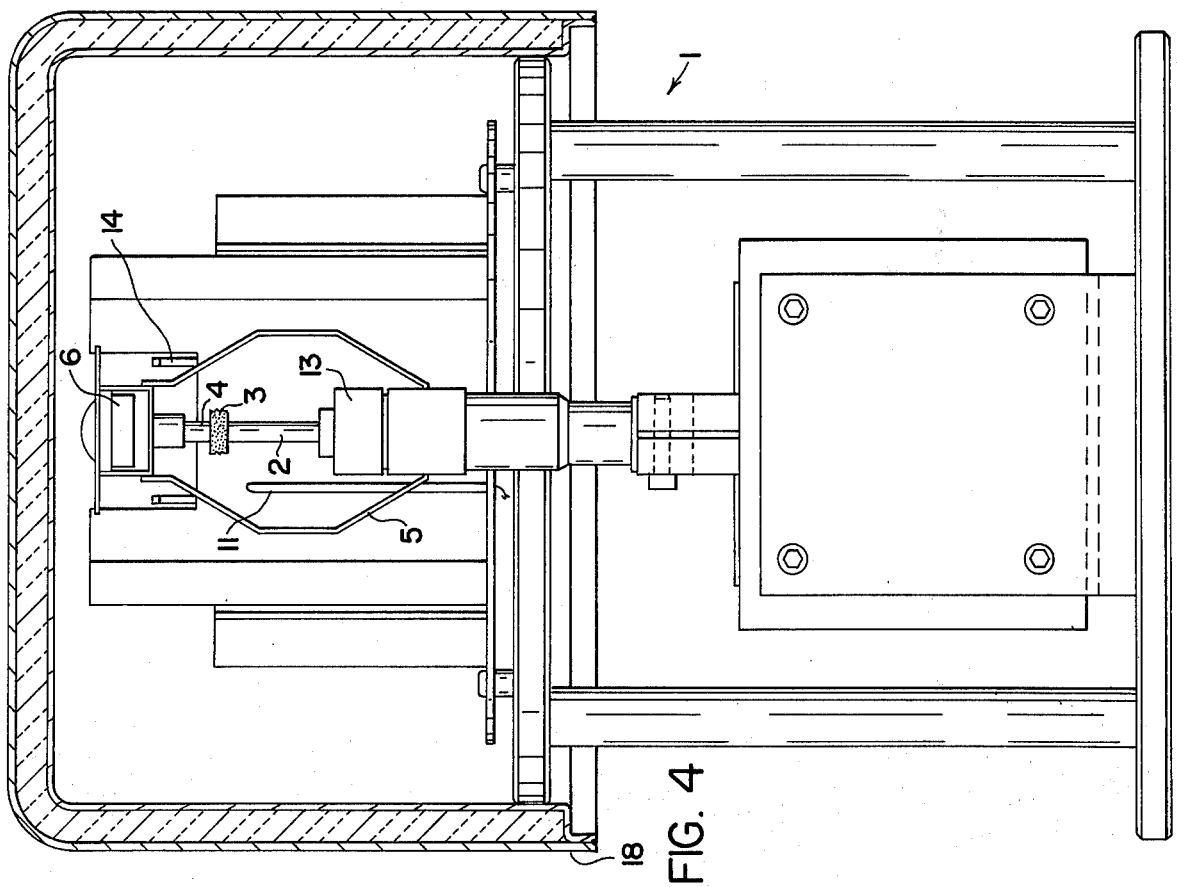

PLASTIC ORIENTATION MEASUREMENT INSTRUMENT

This invention relates to a plastic orientation measurement instrument and more particularly pertains to an apparatus used to measure the degree of orientation in small oriented plastic samples which operates on the principle of measurement of dimensional changes of a sample of plastic during and after the sample passes through the temperature range in which the sample relaxes and becomes unoriented.

The apparatus embodied in this invention is capable of measuring the amount of orientation present in an oriented (stretched) sample of plastic material in either a compression or tension mode. The initial magnitude of compression or tension applied to a given sample of oriented thermoplastic material by the instrument sensor is continuously adjustable from zero up to several grams.

The magnitude of orientation in a stretched sample of a thermoplastic material can be measured with the apparatus of this invention by gradually raising the temperature of the sample and at the same time measuring the dimensional change of the sample as the molecular structure of the sample relaxes. The rate of dimensional change is also measured with our apparatus.

Dimensional change and rate of dimensional change of the sample of oriented thermoplastic material are measured by tracking the thickness of the sample with a mechanical sensor. The sensor is attached to a ring-like structure which is supported by a knife edge at the end of a beam balance which in turn is also supported on a knife edge. The beam balance and sensor support structure are normally caged when the instrument is not in use or is being transported.

The apparatus of this invention is illustrated in the accompanying drawings wherein:

FIG. 4 is a view taken along line 4—4 in FIG. 2.

FIG. 5 is a view taken along line 5—5 in FIG. 2.

Figure 1:
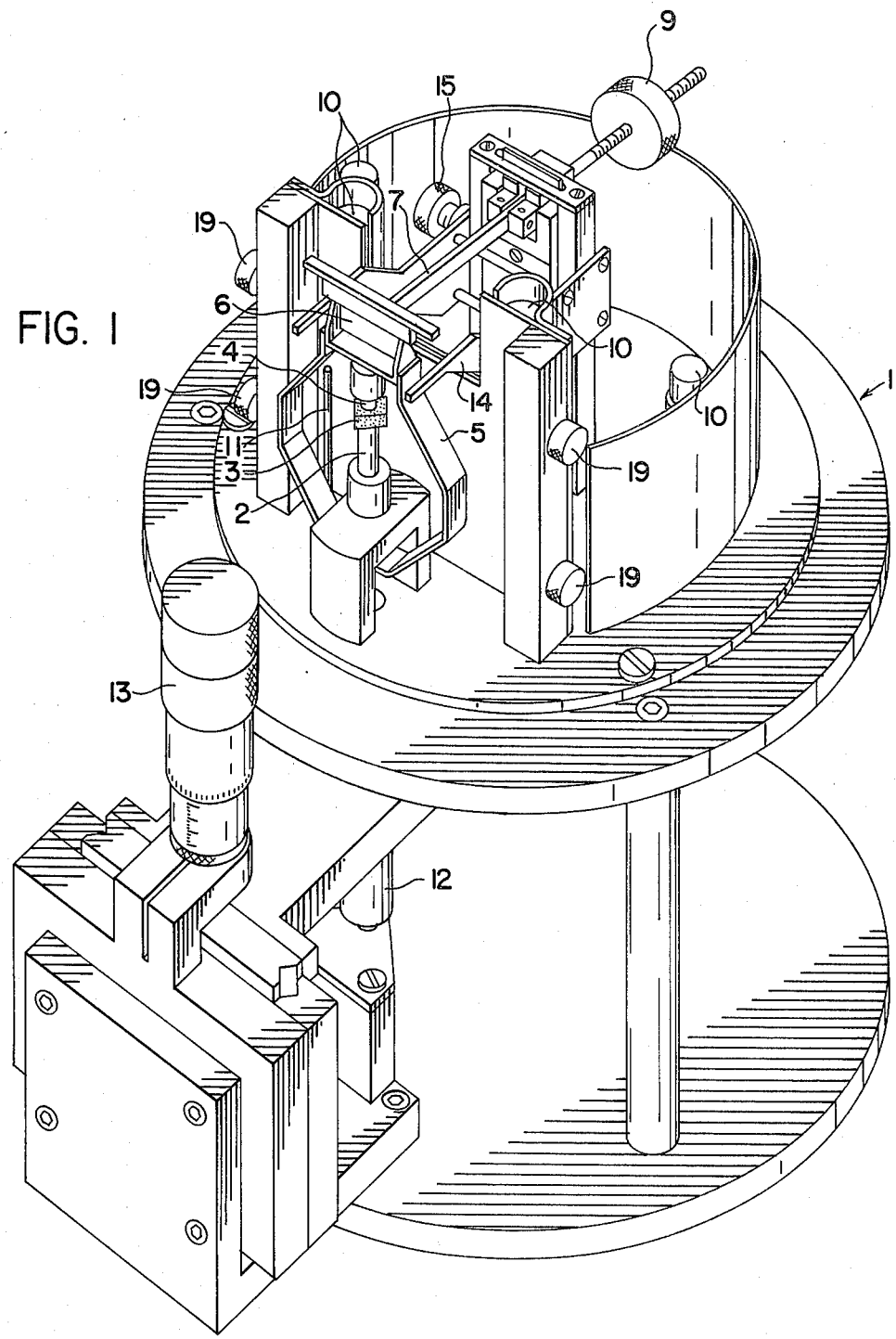
FIG. 1 is a perspective view of the plastic orientation measurement instrument.
Figure 2:
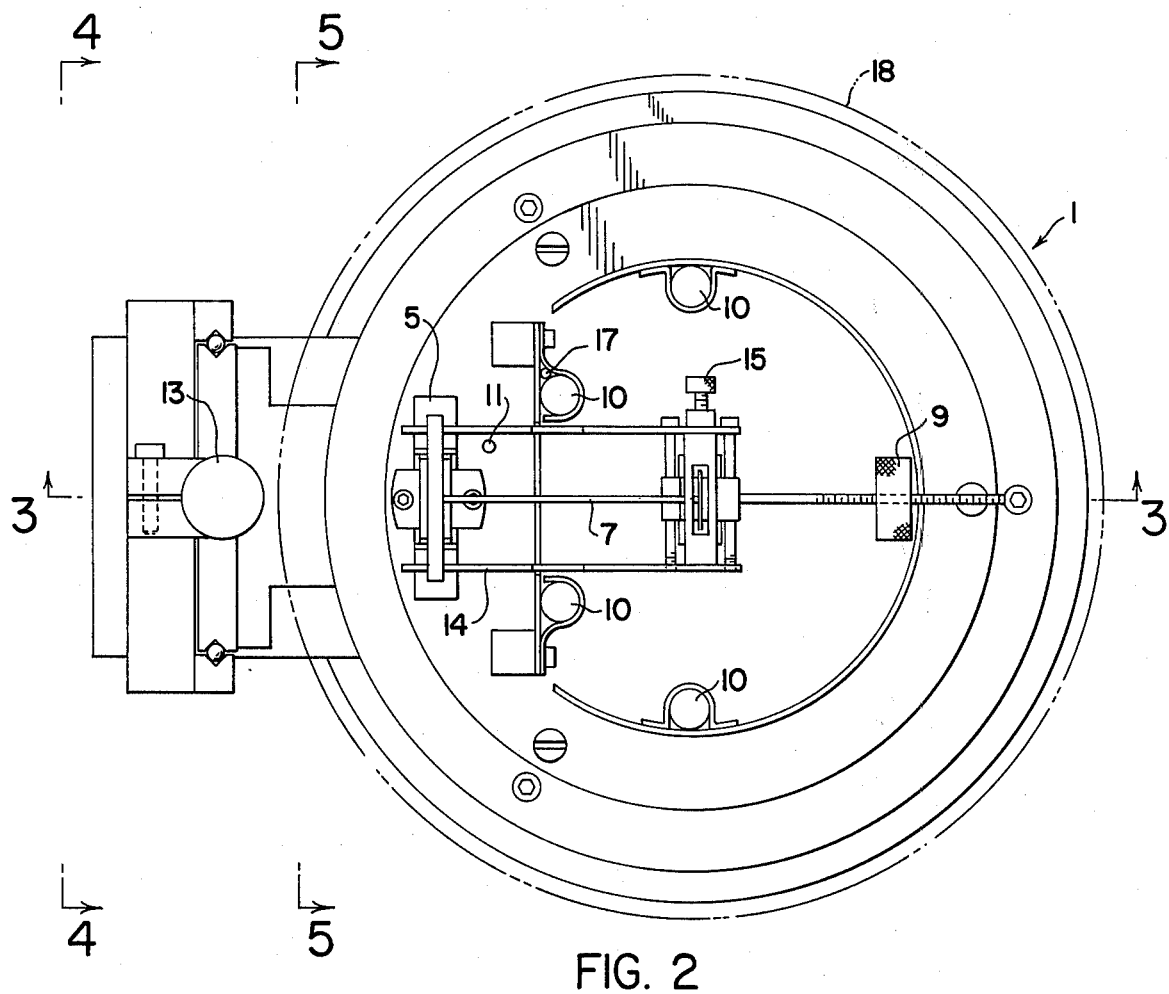
FIG. 2 is a top view partly in section of the instrument.
Figure 3:
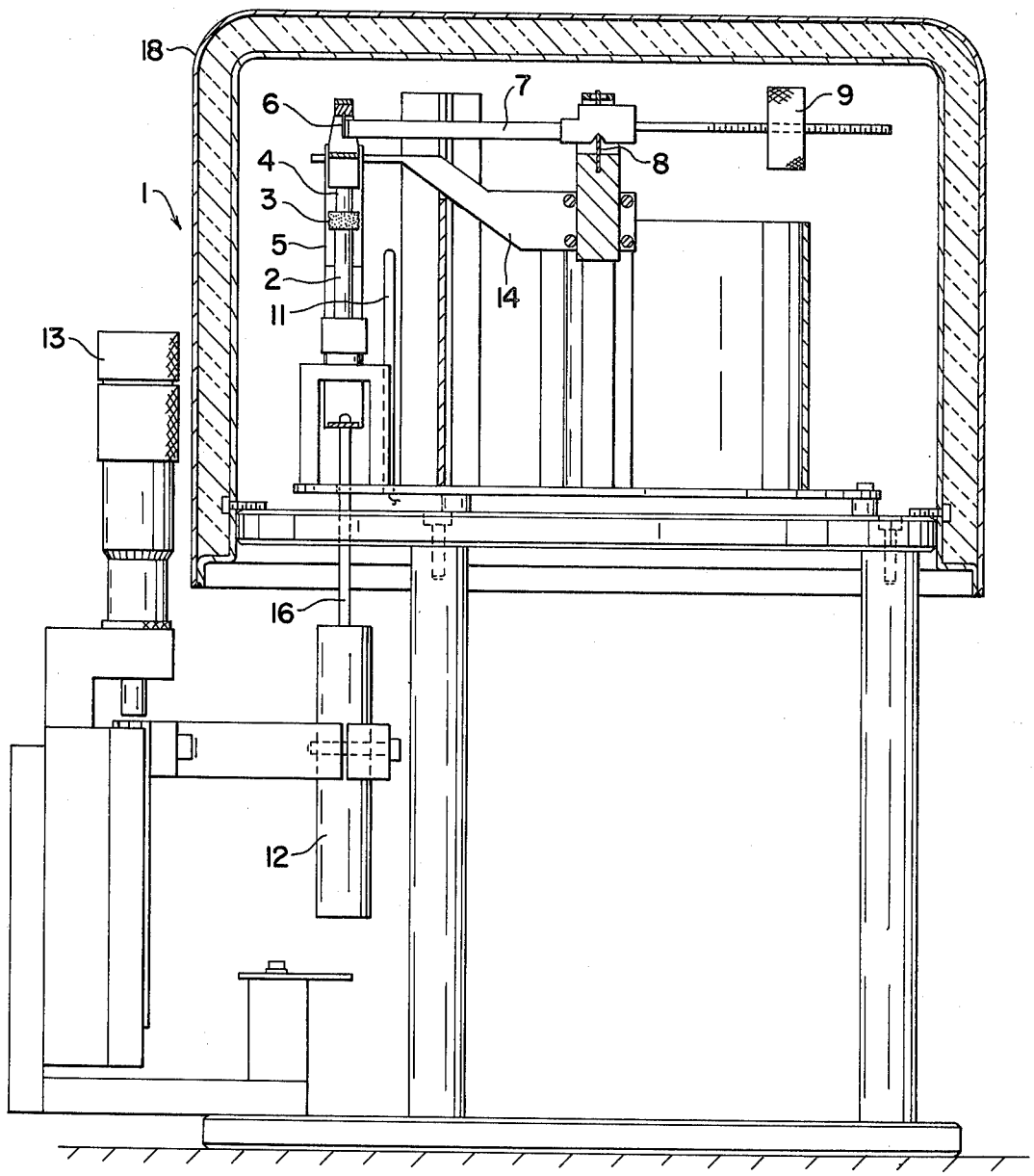
FIG. 3 is a view along line 3—3 in FIG. 2.

The plastic orientation measurement instrument 1 is equipped with a stationary bottom anvil 2 upon which is placed the plastic sample to be tested 3. A top anvil 4 serves as a sensor which is connected to the yoke 5 which is supported by a knife edge 6 located at the end of balance beam 7. The balance beam 7 is balanced on the knife edge 8 located near the middle thereof. At the far end of the balance beam 7 is located a thumb nut 9 for pressure or tension adjustment. The temperature within the apparatus is adjusted by heaters 10 and the temperature near the sample is measured by thermocouple 11. The linear voltage differential transformer (LVDT) 12 measures displacement or movement of the yoke 5. The micrometer screw 13 is used to adjust to zero the initial output of the LVDT. A cage 14 can be either engaged or disengaged by means of thumbscrew 15. The connecting link between the yoke 5 and the LVDT is a thin metal tube 16. A thermocouple 17 controls the heaters 10. An insulated cover 18 is put in place while the apparatus is in operation and thumbscrews 19 are sometimes used to secure a small heat shield (not shown) which surrounds the sample area.

In the operation of the apparatus of this invention, the temperature under which the measurement is made can be monitored by continuous indication of the temperature near the sample as recorded on a meter in either ° C or ° F. The dimensional change of the plastic sample in either expansion along the "z" axis or shrinkage along an "x" or "y" axis is readily recorded on a chart recorder.

Either displacement or the velocity of displacement of dimensional change can be recorded on a chart as related to either sample expansion or shrinkage.

Output terminals are provided so that displacement and velocity can be recorded simultaneously on a two-channel chart recorder.

The apparatus of this invention is portable and can be fitted into a case which is within the maximum allowable dimensional limits for carry-on baggage aboard commercial aircraft.

The sensor loading onto the sample can be adjusted by a thumbscrew on the balance beam in such a manner that loading values ranging from essentially zero to several grams can be applied to the sample. Loading values of about several hundred milligrams have been found to be satisfactory.

The displacement of the sensor as the plastic sample expands or contracts is measured by a linear voltage differential transformer (LVDT). The core of the LVDT is attached by a low thermal conductivity stainless-steel tube to the bottom part of the ring structure which supports the sensor.

The balance beam and the cell which encloses the sample are heated by electric heaters. A thermocouple which contacts one of the heaters is used to sense and control the temperature within the instrument. A second thermocouple measures the temperature near the sample under test and usually indicates this temperature on a meter.

In most instances, the plastic sample after being mounted in the apparatus is enclosed in a small cell which remains closed while the measurement is made. The purpose of the smaller cell around the sample is to minimize thermal convection near the sample and to provide an enclosure around the sample which is more representative of the actual sample temperature during the test.

In the operation of the apparatus of this invention, the measurement of orientation of the plastic sample along the z axis under compression (as shown in the accompanying drawings) or along the x or y axes under tension requires different arrangements for contacting or supporting the sample. For expansion measurement along the z axis (as shown in the accompanying drawings) which places the plastic sample under compression, two cylindrical-type anvils are used. The lower anvil is made of stainless steel and is held by a friction fit and has a spherical tip. The top sensor anvil is made of brass and has a flat tip. The top anvil is the sensor which tracks the expansion of the sample thickness and mechanically communicates this to the LVDT. Loading of the sensor anvil onto the sample and the bottom anvil can easily be adjusted by turning the thumb nut on the beam balance to provide a downward positive loading of several hundred milligrams onto the sample. The magnitude of the loading force is best set by hanging a weight of the proper value on the threaded arm of the beam balance at a distance of 1 and ½ inches from the knife edge and adjusting the thumb nut for balance. The test weight is then removed before the test begins.

When a plastic sample is to be tested for orientation in the x or y axes, it is necessary to replace the anvil holders shown in the accompanying drawings with sample holders which support the sample by spring clips. After the top anvil has been replaced with a spring clip holder, the beam balance must be readjusted from a positive load to a negative load so as to place the sample under tension when it is gripped by the upper and lower spring clips. The magnitude of this tension is adjusted by moving the thumb nut for balance after a weight of the desired loading magnitude has been placed on the beam balance directly over the axis of the spring clip sample holders.

In the actual measurement of the degree of orientation in a plastic sample using the apparatus shown in the accompanying drawings, the oriented plastic material to be tested should be cut into a rectangular piece ranging between 7 × 7 to 10 × 10 mm. The sample thickness is measured with a micrometer, it is recorded and then, after releasing the balance caging apparatus, the sample is placed so that it is centered between the two anvils. The power is then turned on and the LVDT micrometer screw is adjusted so that the recorder reads zero. The cover is then placed over the instrument with care making sure that the threaded rod of the balance is not struck by the cover as it is lowered. The test is then carried out. It should be noted that the instrument is very sensitive to velocity and when such records are taken, the instrument should be placed on a solid surface to minimize vibration.

For measurements in the tension mode, the anvils are removed and the measurement is conducted with the sample supported, under tension, by the spring clips. In this mode, the sample size should be approximately 6 to 7 mm. in width × 14 mm. in length. A tension measurement, sample shrinkage, is usually more difficult to set up than a sample tested for expansion.

Any thermoplastic material which can be oriented can be tested in the apparatus of our invention. Among such thermoplastic materials are included polypropylene, polystyrene, styrene-acrylonitrile copolymers, ABS resins, high nitrile copolymers and rubber-modified high acrylonitrile copolymers, nylons, polyesters, and the like, and others.

The invention is further illustrated in the following example.

EXAMPLE

A 32-ounce biaxially oriented soft-drink bottle was fabricated from Barex ® 210 resin which is a copolymer of about 75 parts by weight of acrylonitrile and about 25 parts by weight of methyl acrylate modified with about 10 parts by weight of a nitrile rubber and is marketed by Vistron Corporation. The bottle was cut into small pieces and some of these pieces were tested for orientation on the apparatus of this invention. The pieces were taken from various parts of the bottle and in each instance represent different degrees of orientation in the plastic.

The sample to be tested was cut into a piece approximately 0.400 inch square. Exact dimensions of each sample were determined by micrometer before and after the test. The test comprises placing the sample in the apparatus and watching the displacement and velocity of displacement as a function of temperature. The temperature rise was 5° C per minute.

The maximum displacement, the maximum velocity achieved and the maximum temperature were recorded. The percent change is based on the micrometer measurements before and after testing. Results run on several samples, each from a different area of the bottle, are given in the table below.

Table

| Sample | Maximum Displacement | Maximum Velocity | Maximum Temperature | % Change Axial | % Change Hoop |
|---|---|---|---|---|---|
| A | 58 mils | 35.3 mils | 95° C | 51.9 | 44.1 |
| B | 90 mils | 41 mils | 100° C | 46.7 | 57.3 |
| C | 76 mils | 15.4 mils | 100° C | 40.4 | 60.3 |
| D | 100 mils | 25.1 mils | 95° C | 44.3 | 51.9 |
| E | 63 mils | 22.8 mils | 95° C | 54.2 | 52.4 |

We claim:

1. An apparatus for measuring dimensional change at elevated temperature in a sample of oriented thermoplastic material comprising means for holding said sample means for heating said sample, sensing means attached to a ring-like structure which is supported by a knife edge at the end of a beam balance which in turn is supported on a knife edge, said means having an essentially zero loading value and being connected to said holding means for sensing and tracking changes in the dimensions of said sample which may take place during the heating of said sample.

2. The apparatus of claim 1 wherein there are also included means for recording temperature change during heating of said sample and also means for recording dimensional change in said sample during the heating of said sample.

3. The apparatus of claim 2 wherein the means for holding the sample comprises a stationary bottom anvil and a movable top anvil.

4. The apparatus of claim 3 wherein the movable top anvil also serves as a sensor of dimensional change in the sample.

* * * * *